(12) United States Patent  
Harding

(10) Patent No.: US 7,492,863 B2
(45) Date of Patent: Feb. 17, 2009

(54) METHOD FOR DEVELOPING AN X-RAY DIFFRACTION IMAGING SYSTEM

(75) Inventor: Geoffrey Harding, Hamburg (DE)

(73) Assignee: GE Security, Inc., Bradenton, FL (US)

( * ) Notice: Subject to any disclaimer, the term of this patent is extended or adjusted under 35 U.S.C. 154(b) by 202 days.

(21) Appl. No.: 11/461,839

(22) Filed: Aug. 2, 2006

(65) Prior Publication Data

US 2008/0031415 A1 Feb. 7, 2008

(51) Int. Cl.
*G01N 23/201* (2006.01)
(52) U.S. Cl. ............... 378/71; 378/98; 378/87
(58) Field of Classification Search ........... 378/70, 378/71, 73, 79, 80, 81, 87, 98, 98.2
See application file for complete search history.

(56) References Cited

U.S. PATENT DOCUMENTS

2005/0002488 A1\* 1/2005 Ozawa et al. ............... 378/87
2005/0190881 A1\* 9/2005 Obata et al. ................. 378/87

OTHER PUBLICATIONS

Geoffrey Harding; "The Design of Direct Tomographic, Energy-Dispersive, X-Ray Diffraction Imaging (XDI) Systems"; Dated Jul. 13, 2005; Presented at SPIE Conference on Aug. 3, 2005; 9 pgs.

\* cited by examiner

*Primary Examiner*—Hoon Song
(74) *Attorney, Agent, or Firm*—Eugene Hyun, Esq.; Armstrong Teasdale LLP

(57) ABSTRACT

A method for developing a virtual representation of an x-ray diffraction imaging system includes generating a symmetry axis, generating a conical shape having a base diameter, a vertex angle α, and a vertex point, locating the vertex point at an origin point on the symmetry axis, and extending a first line and a second line between the vertex point and the conical base such that the first line is separated an angle $d_\phi$ from the second line in an azimuthal direction around the conical base.

24 Claims, 3 Drawing Sheets

METHOD FOR DEVELOPING AN X-RAY DIFFRACTION IMAGING SYSTEM

BACKGROUND OF THE INVENTION

This invention relates generally to x-ray diffraction imaging (XDI) systems, and more particularly to a method of developing an x-ray diffraction imaging system.

The Transportation Security Administration (TSA) has recently mandated more stringent inspection procedures be implemented by the travel industry to reduce the possibility of passengers boarding a carrier such as a plane, for example, carrying concealed weapons, explosives, or other contraband. To facilitate preventing passengers boarding a plane carrying concealed weapons, explosives, etc., the TSA requires that all passengers be screened prior to boarding the aircraft.

One such inspection system utilized to perform the inspection procedures is an x-ray diffraction imaging (XDI) system. Known XDI systems are generally designed utilizing several parameters that include, for example, overall system cost and space constraints. More specifically, the design of the XDI system is typically based on a single primary factor. For example, the XDI system may be designed based on pre-existing space constraints thus causing the cost of the overall system to increase. Moreover, the XDI system may be designed within certain cost restraints while de-emphasizing the space constraints of the system. As a result, known XDI systems may not be designed to optimize all of the design variables, such as the size constraint and the cost.

BRIEF DESCRIPTION OF THE INVENTION

In one aspect, a method for developing a virtual representation of an x-ray diffraction imaging system is provided. The method includes generating a symmetry axis, generating a conical shape having a base diameter, a vertex angle α, and a vertex point, locating the vertex point at an origin point on the symmetry axis, and extending a first line and a second line between the vertex point and the conical base such that the first line is separated by an angle $d_\varphi$ from the second line in an azimuthal direction around the conical base.

In another aspect, a processor for developing a virtual representation of an x-ray diffraction imaging system is provided. The processor is programmed to generate a symmetry axis, generate a conical shape having a base diameter, a vertex angle α, and a vertex point, locate the vertex point at an origin point on the symmetry axis, and extend a first line and a second line between the vertex point and the conical base such that the first line is separated by an angle $d_\varphi$ from the second line in an azimuthal direction around the conical base.

In a further aspect, a computer program for developing a virtual representation of an x-ray diffraction imaging system is provided. The computer program is programmed to generate a symmetry axis, generate a conical shape having a base diameter, a vertex angle α, and a vertex point, locate the vertex point at an origin point on the symmetry axis, and extend a first line and a second line between the vertex point and the conical base such that the first line is separated by an angle $d_\varphi$ from the second line in an azimuthal direction around the conical base.

DETAILED DESCRIPTION OF THE INVENTION

Figure 1:
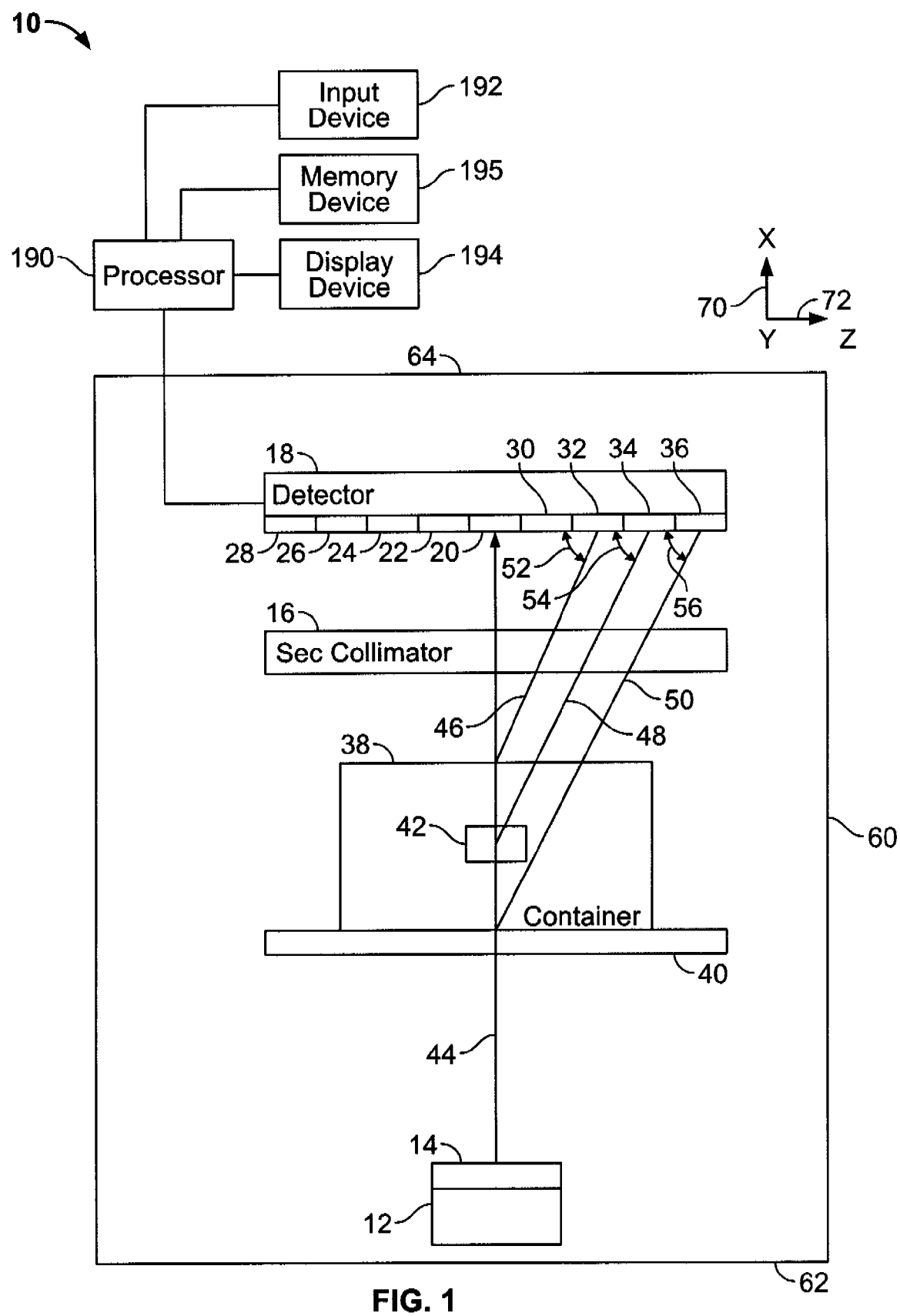
FIG. 1 is a block diagram of an x-ray diffraction imaging system.

FIG. 1 is a block diagram of an exemplary x-ray diffraction imaging (XDI) system 10 for generating a diffraction profile of a substance. System 10 includes an x-ray source 12 that includes a primary collimator 14. System 10 further includes a secondary collimator 16, and a detector 18. Detector 18 includes a central detector element 20 or a central detector cell for detecting primary radiation. Detector 18 also includes a plurality of detector cells or detector elements 22, 24, 26, 28, 30, 32, 34, and 36 for detecting coherent scatter. Detector 18 includes any number, such as, ranging from and including 256 to 1024, of detector elements. A container 38 is placed on a support 40 between x-ray source 12 and detector 18. Examples of container 38 include a bag, a box, and an air cargo container. Examples of x-ray source 12 include a polychromatic x-ray tube. Container 38 includes a substance 42. Examples of substance 42 include an organic explosive, an amorphous substance having a crystallinity of less than twenty five percent, a quasi-amorphous substance having a crystallinity at least equal to twenty-five percent and less than fifty percent, a partially crystalline substance having a crystallinity at least equal to fifty percent and less than one-hundred percent, and a crystalline substance having a crystallinity of one-hundred percent. Examples of the amorphous, quasi-amorphous, and partially crystalline substances include a gel explosive, a slurry explosive, an explosive including ammonium nitrate, and a special nuclear material. Examples of the special nuclear material include plutonium and uranium. Examples of support 40 include a table and a conveyor belt. An example of detector 18 includes a segmented detector fabricated from Germanium.

X-ray source 12 emits x-rays. Using primary collimator 14, a primary beam 44, such as a pencil beam, is formed from the x-rays generated. Primary beam 44 passes through container 38 arranged on support 40 to generate scattered radiation, such as a plurality of scattered rays 46, 48, and 50. Above support 40, there is arranged detector 18, which measures an intensity of primary beam 44 and photon energy of the scattered radiation. Detector 18 measures the x-rays in an energy-sensitive manner by outputting a plurality of electrical output signals linearly dependent on a plurality of energies of x-ray quanta detected from within primary beam 44 and the scattered radiation.

Detector elements 20, 22, 24, 26, 28, 30, 32, 34, and 36 are geometrically arranged so that an incident angle of the scatter radiation detected by each detector element 20, 22, 24, 26, 28, 30, 32, 34, and 36 is constant. For example, an angle 52 at which scattered ray 46 is incident on detector element 32 is equal to an angle 54 at which scattered ray 48 is incident on detector element 34 and an angle 54 is equal to an angle 56 at which scattered ray 50 is incident on detector element 36. As another example, scattered ray 46 is parallel to scattered rays 48 and 50. Central detector element 20 measures an energy or alternatively an intensity of primary beam 44 after primary beam 44 passes through container 38. Detector elements 22, 24, 26, 28, 30, 32, 34, and 36 separately detect the scattered radiation received from container 38.

Secondary collimator 16 is located between support 40 and detector 18. Secondary collimator 16 includes a number of collimator elements, such as sheets, slits, or laminations, to ensure that the scatter radiation arriving at detector 18 have constant scatter angles and that a position of detector 18 permits a depth in container 38 at which the scatter radiation originated to be determined. The number of collimator elements provided is equal to or alternatively greater than a number of detector elements 20, 22, 24, 26, 28, 30, 32, 34, and 36 and the collimator elements are arranged such that the scattered radiation between neighboring collimator elements each time is incident on one of the detector elements 22, 24, 26, 28, 30, 32, 34, and 36. The collimator elements are made of a radiation-absorbing material, such as, a copper alloy or a silver alloy. In one embodiment employing a fan-beam geometry, a plurality of origination points, within container 38, of the scatter radiation are detected by the detector elements 22, 24, 26, and 28, aligned in a first direction and detector elements 30, 32, 34, and 36 aligned in a second direction that is opposite to and parallel to the first direction. Detector 18 detects the scattered radiation to generate a plurality of electrical output signals. In an alternative embodiment, system 10 does not include primary and secondary collimators 14 and 16.

In the exemplary embodiment, system 10 is housed within an enclosure 60, such as a room or gantry. For example, in the exemplary embodiment shown in FIG. 1, source 12 is located proximate to a floor 62 of enclosure 60 and detector 18 is located proximate to a ceiling 64 of enclosure 60. In this arrangement, the source 12 and detector 18 are each arranged along a symmetry axis (x), in this case a vertical axis 70 with respect to enclosure 60 such that source 12 is positioned a first distance from floor 62 and detector 18 is positioned a second distance that is greater than the first distance from floor 62. In another embodiment, not shown, source 12 and detector 18 are each arranged along a symmetry axis (y) in this case a horizontal axis 72 with respect to enclosure 60 such that source 12 and detector 18 are each positioned the same distance from floor 62. Optionally, source 12 and detector 18 may be positioned in a wide variety of alignments within enclosure 60 without affecting the scope of the invention described herein.

System 10 also includes a processor 190, an input device 192, a display device 194, and a memory device 195. As used herein, the term processor is not limited to just those integrated circuits referred to in the art as a processor, but broadly refers to a computer, a microcontroller, a microcomputer, a programmable logic controller, an application specific integrated circuit, and any other programmable circuit. The computer may include a device, such as, a floppy disk drive or CD-ROM drive, for reading data including the methods for determining an atomic number of a substance from a computer-readable medium, such as a floppy disk, a compact disc-read only memory (CD-ROM), a magneto-optical disk (MOD), or a digital versatile disc (DVD). In another embodiment, processor 190 executes instructions stored in firmware. Examples of display device 194 include a liquid crystal display (LCD) and a cathode ray tube (CRT). Examples of input device 192 include a mouse and a keyboard. Examples of memory device 195 include a random access memory (RAM) and a read-only memory (ROM).

Figure 2:
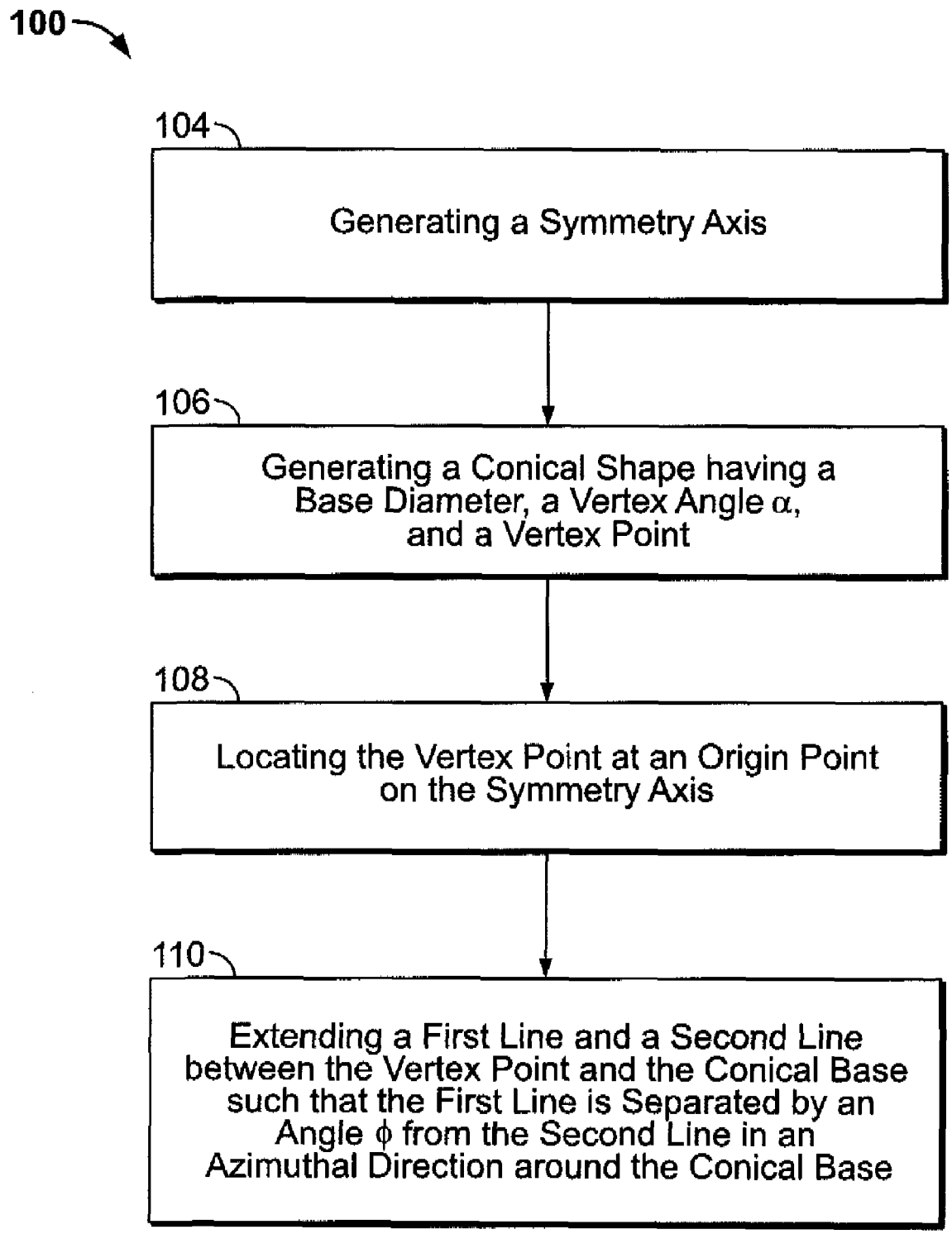
FIG. 2 is a flow chart illustrating an exemplary method of developing an x-ray diffraction imaging system.
Figure 3:
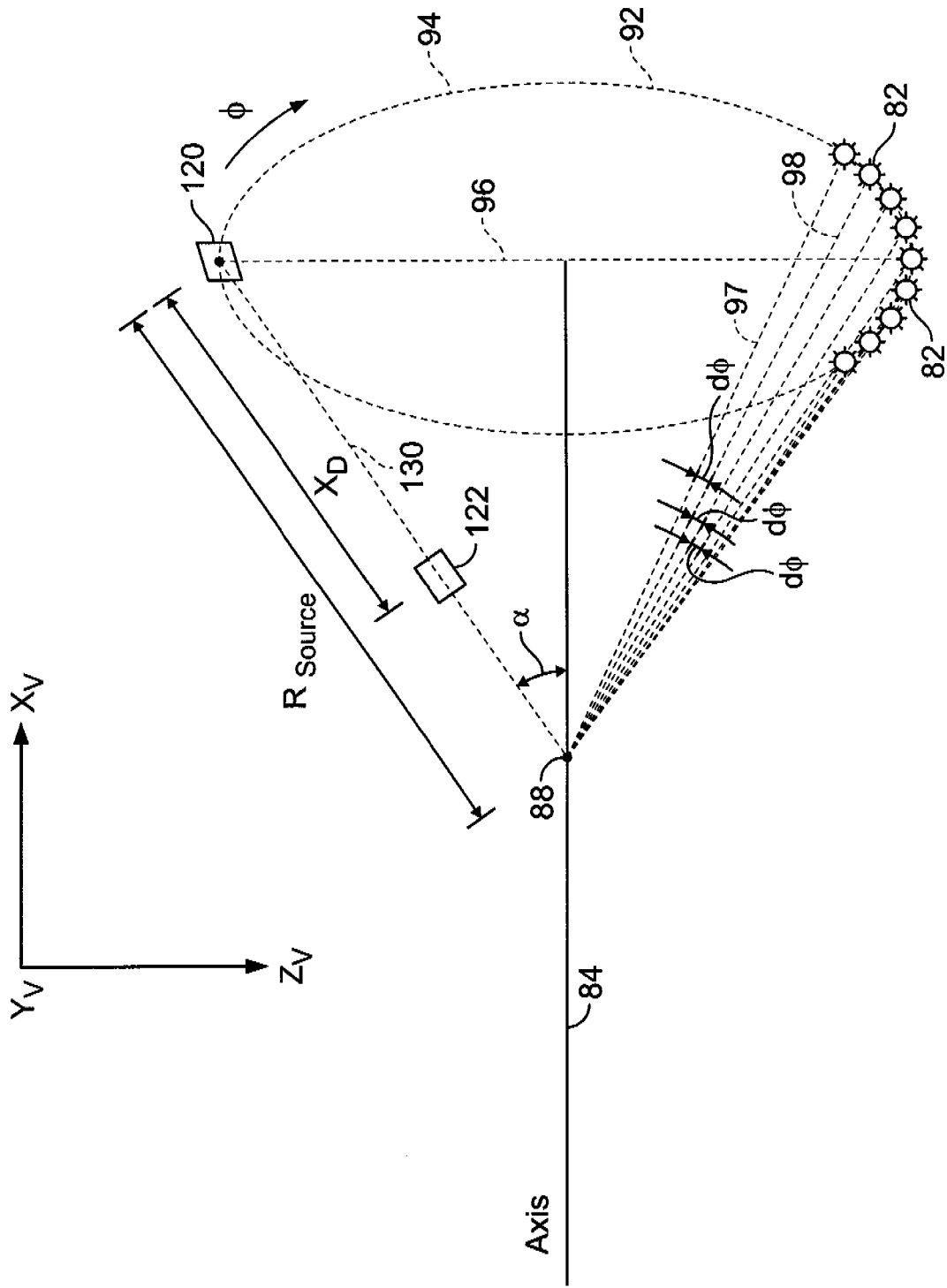
FIG. 3 is a perspective view of an exemplary XDI system that is developed utilizing method shown in FIG. 2.

FIG. 2 illustrates an exemplary method 100 that is executed by processor 190 for developing an XDI system such as system 10 shown in FIG. 1. FIG. 3 is a perspective view of an exemplary XDI system that is developed or created utilizing the method shown in FIG. 2.

Specifically, during the development process of an XDI system, such as system 10, it can be shown that an arbitrary, elemental, primary "pencil beam" ray in a three-dimensional (3-D) tomographic XDI system can be derived from a generic two-dimensional (2-D) geometry incorporating three additional or arbitrary parameters. These parameters include a vertex angle ($\alpha$), an azimuthal angle ($\phi$), and an intersection coordinate ($R_{source}$). In the development procedure described herein, each of the three parameters may vary in one and the same 3-D tomographic XDI system if a pixellated detector array is available. Moreover, temporal variation of these three parameters may be utilized in the development procedure.

In the exemplary embodiment, processor 190 develops an XDI system by creating 102 a virtual representation of the XDI system by generating 104 a symmetry axis 84, generating 106 a conical shape 92 having a base 94, a base diameter 96, and a vertex point 88, locating 108 the vertex point 88 on the symmetry axis 84, and extending 110 a line 97 and a line 98 from the vertex point 88 to the conical base 94 such that line 97 is separated at an angle $d_\phi$ from line 98 in an azimuthal direction $\phi$ around the conical base 94. Processor 190 extends any number of lines, such as 4, 5, 6, etc., from vertex point 88 to conical base 94 based on an input of the number of lines provided by a person via input device 192. Processor 190 forms a vertex angle $\alpha$ between a surface of the conical shape and the symmetry axis 84. Processor 190 generates symmetry axis 84 and the conical surface to pass symmetry axis 84 through vertex point 88 and a center of base 94.

Processor 190 places a virtual representation 120 of x-ray source 12 along line 97 at a distance $R_{source}$ from vertex point 88. Moreover, processor 190 may place additional virtual representations 120 of x-ray source 12 along lines extending from vertex point 88 to conical base 94. For example, processor 190 may place along a line 130 a virtual representation 120 of x-ray source 12 at the distance $R_{source}$ from vertex point 88. The vertex angle $\alpha$ is formed between symmetry axis 84 and any of the lines, such as lines 97 and 98, for example, extending between the vertex point 88 and the conical base 94. Processor 190 places a virtual representation 122 of a detector element or cell 18 at a distance $X_D$ from virtual representation 120 along a line on which virtual representation 120 is generated. For example, processor 190 generates virtual representation 122 of detector 18 at the distance $X_D$ along line 130 when processor 190 generates a virtual representation 120 of x-ray source 12 at the distance $R_{source}$ along line 130. As another example, processor 190 places virtual representation 120 of x-ray source 12 at vertex point 88 on line 130 and places virtual representation 122 of detector 18 at the distance $X_D$ from virtual representation 120 along line 130. As yet another example, processor 190 generates virtual representation 122 on line 97 upon generating virtual representation 120 on line 97.

In one exemplary embodiment, the distance $R_{source}$ is not equal to zero. For example, the distance $R_{source}$ ranges from $-\infty$, such as $-1000$ kilometers, from vertex point 88 in a direction away from base 94 to $+\infty$, such as $+1000$ kilometers, from vertex point 88 in a direction towards base 94. Optionally, the distance $R_{source}$ is equal to zero. In another exemplary embodiment, the distance $R_{source}$ is not equal to negative infinity from the vertex point 88. Optionally, the distance $R_{source}$ is equal to negative infinity, such as between 100 and 200 meters, from the vertex point 88. In another exemplary embodiment, the distance $R_{source}$ is not equal to a distance between the vertex point and the conical base. Optionally, the distance $R_{source}$ is equal to the distance $X_D$. In one exemplary embodiment, the distance $R_{source}$ from the vertex point 88 is not equal to zero, and the vertex angle $\alpha$ is not equal to zero. Optionally, the distance $R_{source}$ from the vertex point 88 is equal to zero, and the vertex angle $\alpha$ is equal to zero. In another exemplary embodiment, the distance $R_{source}$ from the vertex point 88 is not equal to zero, the vertex angle $\alpha$ is not equal to ninety degrees. Optionally, the distance $R_{source}$ from the vertex point 88 is equal to zero, and the vertex angle $\alpha$ is equal to ninety degrees. Processor 190 receives the distance $R_{source}$, the distance $X_D$, and the vertex angle α from the person via input device 192. The user fabricates an XDI system, such as system 10, based on a virtual representation, illustrated in FIG. 3. For example, the user manufactures source 12 and detector 18 to place source 12 at a first distance from detector 18. The first distance is proportional, such as four or fives times, a second distance between virtual representation 120 and virtual representation 122.

In general, the most complex components of an x-ray diffraction imaging (XDI) system, such as system 10, are the x-ray source 12 and the detector array 18. Specifically, the cost of detector array 18 is generally proportional to its area, and the cost of x-ray source 12 of given power scales is approximately in inverse proportion to its focus area. Technical effects of the herein described method 100 is to develop a virtual representation of an x-ray diffraction imaging (XDI) system to optimize the geometrical factors affecting the size and shape of both x-ray source 12 and detector array 18.

Method 100 may be utilized to develop three XDI systems, i.e. "Direct Fanbeam", "Inverse Fanbeam", and "Parallel Beam". An XDI imaging system may be developed with a point source and a large detector (Direct Fan), or with a point detector and a large source (Inverse Fan), or with a moderate sized detector and a moderate sized source. Since known radiation detectors are generally more costly than known radiation sources, the method of developing an exemplary XDI system described herein is utilized to design an XDI system having a relatively small detector and one or more radiation sources to facilitate reducing cost of XDI system.

Described herein is a method for developing an XDI system that is characterized by a generic 2-D section extended to 3-D by specifying three geometrical parameters α, $R_{source}$, and φ. Although α, $R_{source}$, and φ have been modified to generate the exemplary systems described herein, it should be realized that α, $R_{source}$, and φ may be modified to produce a wide variety of XDI system designs, including, but not limited to the Direct Fan and Inverse Fan designs described above.

While the invention has been described in terms of various specific embodiments, those skilled in the art will recognize that the invention can be practiced with modification within the spirit and scope of the claims.

What is claimed is:

1. A method for developing a virtual representation of an x-ray diffraction imaging system, said method comprising:
    generating a symmetry axis;
    generating a conical shape having a base, a base diameter, a vertex angle α, and a vertex point;
    locating the vertex point at an origin point on the symmetry axis;
    extending a first line and a second line between the origin point and the base such that the first line is separated by an angle $d_φ$ from the second line in an azimuthal direction around the base; and
    displaying the virtual representation of the x-ray diffraction imaging system to a user.

2. A method in accordance with claim 1 wherein generating a symmetry axis further comprises generating a symmetry axis that passes through the vertex point and a center of the base diameter.

3. The method in accordance with claim 1, further comprising locating a position of an x-ray source at a distance $R_{source}$ from the vertex point along the first line.

4. The method in accordance with claim 3 wherein the distance $R_{source}$ is not equal to zero.

5. The method in accordance with claim 3 wherein the distance $R_{source}$ is not equal to negative infinity from the vertex point.

6. The method in accordance with claim 3 wherein the distance $R_{source}$ is not equal to a distance between the position of the x-ray source and a position of the x-ray detector.

7. The method in accordance with claim 3 wherein when the distance $R_{source}$ from the vertex point is not equal to zero, the vertex angle α is not equal to zero.

8. The method in accordance with claim 3 wherein when the distance $R_{source}$ from the vertex point is not equal to zero, the vertex angle α is not equal to ninety degrees.

9. A processor for developing a virtual representation of an x-ray diffraction imaging system, said processor programmed to:
    generate a symmetry axis;
    generate a conical shape having a base, a base diameter, a vertex angle α, and a vertex point;
    locate the vertex point at an origin point on the symmetry axis;
    extend a first line and a second line between the origin point and the base such that the first line is separated by an angle $d_φ$ from the second line in an azimuthal direction around the base; and
    displaying the virtual representation of the x-ray diffraction imaging system to a user.

10. A processor in accordance with claim 9 wherein to generate a symmetry axis, said processor further programmed to generate a symmetry axis that passes through the vertex point and a center of the base diameter.

11. A processor in accordance with claim 9 further programmed to locate a position of an x-ray source at a distance $R_{source}$ from the vertex point along the first line.

12. A processor in accordance with claim 11 further programmed to locate a position of an x-ray source at a distance $R_{source}$ from the vertex point along at least one of the first and second lines, wherein the distance $R_{source}$ is not equal to zero.

13. A processor in accordance with claim 11 further programmed to locate a position of an x-ray source at a distance $R_{source}$ from the vertex point along at least one of the first and second lines, wherein the distance $R_{source}$ is not equal to negative infinity from the vertex point.

14. A processor in accordance with claim 11 further programmed to locate a position of an x-ray source at a distance $R_{source}$ from the vertex point along one of the first and second lines, wherein the distance $R_{source}$ is not equal to a distance between the position of the x-ray source and a position of the x-ray detector.

15. A processor in accordance with claim 11 further programmed to define an angle α between a primary beam radiated from an x-ray source location and the axis of symmetry, wherein when the distance $R_{source}$ from the vertex point is not equal to zero, the vertex angle α is not equal to zero.

16. A processor in accordance with claim 11 further programmed to define an angle α between a primary beam radiated from an x-ray source location and the axis of symmetry, wherein when the distance $R_{source}$ from the vertex point is not equal to zero, the vertex angle α is not equal to ninety degrees.

17. A computer program embedded on a computer readable medium for developing a virtual representation of an x-ray diffraction imaging system, said computer program comprising at least one code segment to:
    generate a symmetry axis;
    generate a conical shape having a base, base diameter, a vertex angle α, and a vertex point;
    locate the vertex point at an origin point on the symmetry axis;

extend a first line and a second line between the origin point and the base such that the first line is separated by an angle $d_\phi$ from the second line in an azimuthal direction around the base; and displaying the virtual representation of the x-ray diffraction imaging system to a user.

18. A computer program in accordance with claim 17 wherein to generate a symmetry axis, said computer program further comprising at least one code segment to generate a symmetry axis that passes through the vertex point and a center of the base diameter.

19. A computer program in accordance with claim 18 further comprising at least one code segment to locate a position of an x-ray source at a distance $R_{source}$ from the vertex point along the first line.

20. A computer program with claim 19 further comprising at least one code segment to locate a position of an x-ray source at a distance $R_{source}$ from the vertex point along at least one of the first and second lines, wherein the distance $R_{source}$ is not equal to zero.

21. A computer program in accordance with claim 19 further comprising at least one code segment to locate a position of an x-ray source at a distance $R_{source}$ from the vertex point along at least one of the first and second lines, wherein the distance $R_{source}$ is not equal to negative infinity from the vertex point.

22. A computer program in accordance with claim 19 further comprising at least one code segment to locate a position of an x-ray source at a distance $R_{source}$ from the vertex point along at least one of the first and second lines, wherein the distance $R_{source}$ is not equal to a distance between the position of the x-ray source and a position of the x-ray detector.

23. A computer program in accordance with claim 19 further comprising at least one code segment to define an angle $\alpha$ between a primary beam radiated from an x-ray source location and the axis of symmetry, wherein when the distance $R_{source}$ from the vertex point is not equal to zero, the vertex angle $\alpha$ is not equal to zero.

24. A computer program in accordance with claim 19 further comprising at least one code segment to define an angle $\alpha$ between a primary beam radiated from an x-ray source location and the axis of symmetry, wherein when the distance $R_{source}$ from the vertex point is not equal to zero, the vertex angle $\alpha$ is not equal to ninety degrees.

* * * * *